(12) United States Patent
Barber

(10) Patent No.: US 6,387,111 B1
(45) Date of Patent: May 14, 2002

(54) METHOD OF USING A MENISCAL VASCULAR PUNCH

(75) Inventor: F. Alan Barber, Frisco, TX (US)

(73) Assignee: Arthrex, Inc., Naples, FL (US)

( * ) Notice: Subject to any disclaimer, the term of this patent is extended or adjusted under 35 U.S.C. 154(b) by 0 days.

(21) Appl. No.: 09/473,959

(22) Filed: Dec. 29, 1999

Related U.S. Application Data

(60) Provisional application No. 60/114,723, filed on Dec. 31, 1998.

(51) Int. Cl.⁷ .................................................. A61B 17/32
(52) U.S. Cl. .............................................. 606/184
(58) Field of Search ........................... 606/1, 184, 566, 606/567; 128/898

(56) References Cited

U.S. PATENT DOCUMENTS 6,171,303 B1 * 1/2001 Ben-Haim et al. ............. 606/15

* cited by examiner

Primary Examiner—Michael H. Thaler
(74) Attorney, Agent, or Firm—Dickstein Shapiro Morin & Oshinsky, LLP

(57) ABSTRACT

A method of meniscal repair promotes the healing of avascular meniscal tears undergoing repair. At least one vascular channel is formed from the white zone to the periphery of the meniscus by removing a cylinder of the meniscus. The approximately 1.5–2 mm channel remains open to allow vascularity to the avascular meniscus.

11 Claims, 3 Drawing Sheets

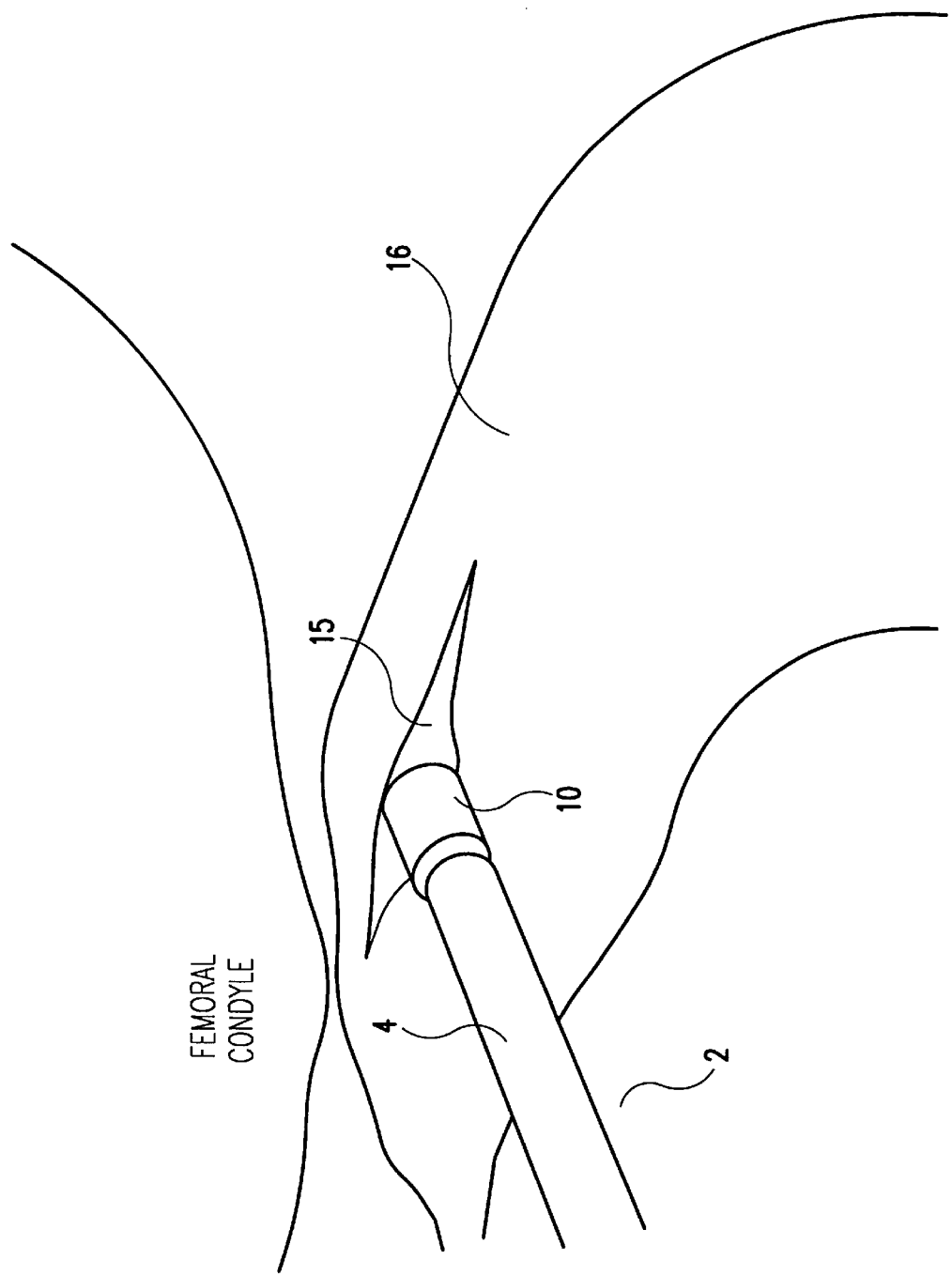

METHOD OF USING A MENISCAL VASCULAR PUNCH

This application claims the benefit of U.S. Provisional Application Serial No. 60/114,723 filed Dec. 31, 1998, the disclosure of which is incorporated herein by reference.

BACKGROUND OF THE INVENTION

1. Field of the Invention

The present invention relates to methods and instruments of meniscal repair. More specifically, the present invention relates to methods and instruments for promoting healing in meniscal repair procedures by forming open channels in the meniscal periphery to increase clot formation in a meniscal tear.

2. Description of the Related Art

The menisci of the knee are two crescent shaped lamellae on the head of the tibia that receive the femoral condyles, laterally and medially, respectively. The surfaces of the menisci are smooth. The inner portion of each meniscus, known as the 'white zone,' is avascular.

Arthroscopic surgical procedures for treating meniscal pathology are becoming increasingly more common. Meniscal tears can be repaired, for example, using the devices and techniques disclosed in pending U.S. patent application Ser. No. 09/099,869, filed Jun. 19, 1998, now U.S. Pat. No. 6,056,778 the entire disclosure of which is incorporated herein by reference. Methods and instrumentation for stimulating the healing response of the menisci and reducing clinical failure are lacking in the known art.

SUMMARY OF THE INVENTION

The present invention provides methods and instrumentation for promoting the healing of avascular meniscal tears, and reducing the clinical failure rate associated with meniscal tears.

According to a preferred method of the present invention, at least one vascular channel is formed from the avascular white zone toward the vascular periphery of the meniscus by removing a cylinder of the meniscus. The channel is formed to a depth sufficient to allow blood to flow from the vascular periphery of the meniscus to the white zone. The channel has a diameter sufficient to remain open during healing of the tear.

A preferred instrument according to the present invention is a meniscal punch with a cannulated handle attached to a cannulated cutting tube. The cutting tube has a sharp distal end used to trephine a meniscal core. A depth stop prevents over-insertion of the punch. Formations on the inside of the cutting tube near the distal cutting end enhance retention of the core within the punch. Suction tubing attached to the back of the punch extracts the core by aspiration. Preferably the formed channels are at least about 1.5–2 mm in diameter, to prevent closing during healing of the repaired meniscal tissue.

The meniscal vascular punch and method of the present invention allows the creation of a bleeding environment in a meniscal tear prior to repair. Forming the open channel by inserting the punch through the tear and into the meniscal periphery increases clot formation within the tear. The core of meniscal tissue can be removed by attaching the vascular punch to suction during penetration and removal.

Other features and advantages of the present invention will become apparent from the following description of the invention which refers to the accompanying drawings.

BRIEF DESCRIPTION OF THE DRAWINGS

FIG. 7 is a schematic representation illustrating a step in a preferred method according to the present invention.

DETAILED DESCRIPTION OF THE PREFERRED EMBODIMENT

Figure 1:
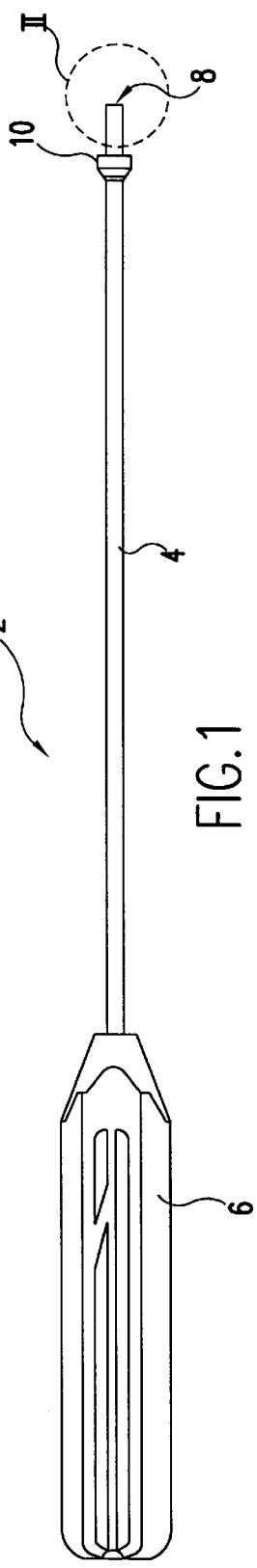
FIG. 1 shows a vascular punch according to the present invention.

Referring to FIG. 1, a meniscal vascular punch 2 according to the present invention is shown. The punch 2 includes a cannulated tube 4 provided on a proximal end with a handle 6. The distal end of tube 4 has a sharp cutting edge 8 and a depth stop 10.

Figure 4:
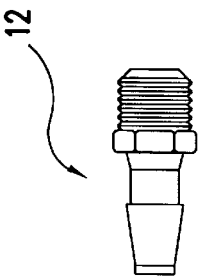
FIG. 4 is a side view of a hose barb for connection of a vacuum supply to the proximal end of the handle of the vascular punch shown in FIG. 1.
Figure 3:
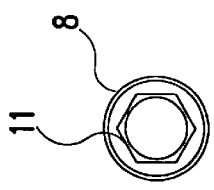
FIG. 3 is an enlarged end view of the distal end of the vascular punch shown in FIG. 1.
Figure 2:
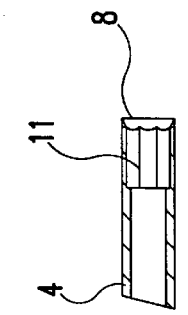
FIG. 2 is an enlarged cross-sectional view of the distal end of the vascular punch shown in FIG. 1.

Referring to FIGS. 2 and 3, the sharp cutting edge 8 at the distal end of the tube 4 is adjoined internally by a hexagonal section 11. Advantageously, the hexagonal section 11 grips a meniscal plug trephined by the sharp edge 8 and helps to retain the plug within the punch, as explained more fully below. The plug also is retained within the punch by a vacuum applied using a hose barb 12 provided on the proximal end of cannulated handle 6. See FIG. 4.

Figure 5:
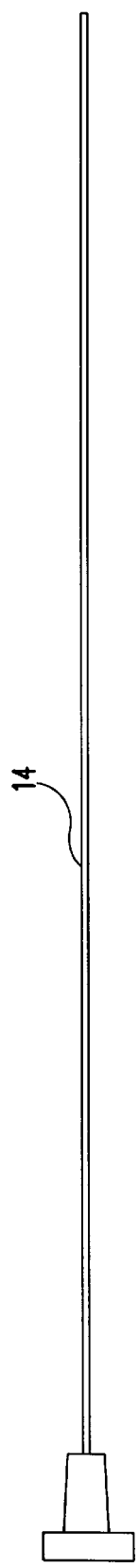
FIG. 5 shows an obturator for use with the vascular punch of FIG. 1.

Referring to FIG. 5, an obturator 14 received within the cannula of tube 4 occludes the distal opening of the tube during introduction of the punch into the knee joint area, to avoid inadvertent damage to non-target tissues. In addition, obturator 14 can be used to clear the trephined meniscal plug from the punch once it is removed from the operative site.

Figure 6:
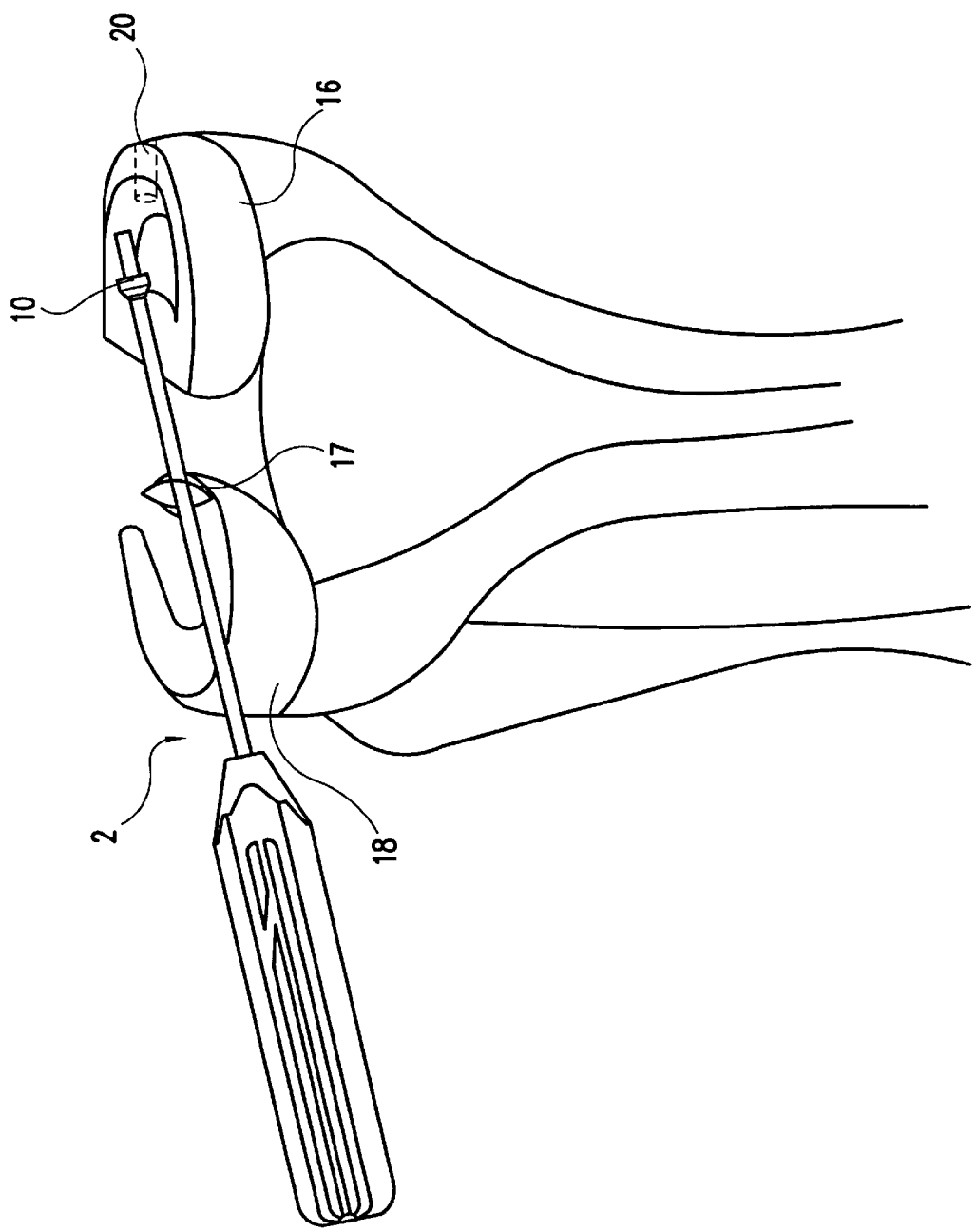
FIG. 6 is a schematic showing the menisci of the right tibia and illustrating a preferred method according to the present invention.

FIGS. 6 and 7 represent schematically a preferred method of promoting the healing of an avascular meniscal tear 15 according to the present invention. At least one vascular channel is formed from the white zone toward the periphery of the medial meniscus 16 by removing a cylinder of the meniscus. Referring more specifically to FIG. 7, the punch 2 is shown having been introduced through an arthroscopy portal 17 (see FIG. 6) and into the tear 15 and toward the medial meniscus to trephine the meniscal core. A similar procedure could be used to treat the lateral meniscus 18.

The cutting end of the punch 2 is inserted through the tear and into the medial meniscus up to the depth stop 10. Prior to insertion into the meniscus, the obturator 14 is retrograded to allow trephining of the meniscal tissue. A vacuum source optionally connected to hose barb 12 of the punch aspirates the meniscal core. A channel 20 approximately 1.5–2 mm in diameter is shown as having been formed in lateral meniscus 16 according to the present invention.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A method of meniscal repair comprising promoting the healing of avascular tissue in a meniscal tear by forming at least one vascular channel from the avascular white zone of the meniscal tissue of the tear toward the periphery of the meniscus to increase clot formation within the tear, the vascular channel being formed by removing a cylinder of the meniscal tissue, the channel remaining open to allow vascularity to the avascular white zone.

2. The method of claim 1, wherein the channel has a diameter of at least about 1.5 mm.

3. The method of claim 1, wherein the channel has a diameter of at least about 2 mm.

4. A method of meniscal repair comprising promoting the healing of avascular tissue in a meniscal tear by forming at least one vascular channel from the avascular white zone of the meniscal tissue of the tear toward the periphery of the meniscus by removing a cylinder of the meniscal tissue using a meniscal punch having a cannulated handle attached to a cannulated cutting tube, the cutting tube having a sharp distal end for trephining a meniscal core, and a depth stop for preventing over-insertion of the punch, the channel remaining open to allow vascularity to the avascular white zone.

5. The method of claim 4, wherein the meniscal punch further comprises formations on the inside of the cutting tube near the distal cutting end for enhancing retention of the core within the punch.

6. The method of claim 4, wherein the meniscal punch further comprises suction tubing attached to the back of the punch for extracting the core by aspiration.

7. A method of meniscal repair comprising the steps of:
introducing a punch through an arthroscopy portal in the knee;
advancing the punch into a meniscal tear toward the meniscus; and
trephining at least one meniscal core to form a vascular channel from the avascular white zone of the meniscal tissue toward the periphery of the meniscus, the channel remaining open to allow vascularity to the avascular white zone of the meniscal tissue, for promoting the healing of the meniscal tear.

8. The method of claim 7, further comprising the step of advancing the punch into the avascular white zone up to a depth established by a depth stop on the punch.

9. The method of claim 7, wherein the punch is fully cannulated, and the method further comprises the step of aspirating the at least one meniscal core using the punch.

10. The method of claim 7, wherein the punch includes an obturator, and the step of introducing the punch into the knee comprises advancing the punch into the meniscal tear toward the medial meniscus with the obturator in place, and removing the obturator prior to trephining the core.

11. The method of claim 7, further comprising forming clots in the tear.

\* \* \* \* \*